United States Patent [19]
Nagamatsu et al.

[11] Patent Number: 5,948,832
[45] Date of Patent: *Sep. 7, 1999

[54] RESIN COMPOSITION HAVING ACTIVE COMPOUND AND VAPORIZABLE PLASTICIZER, AND MOLDED PRODUCT THEREOF

[75] Inventors: Tatsuhiro Nagamatsu, Takatsuki; Hiroki Nakata, Toyonaka; Takanori Kume, Ichihara; Tadashi Sakurai, Uji, all of Japan

[73] Assignee: Sumitomo Chemical Company, Limited, Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/677,118

[22] Filed: Jul. 9, 1996

[30] Foreign Application Priority Data

Jul. 10, 1995 [JP] Japan ..................... 7-173411

[51] Int. Cl.⁶ .......................... A61K 31/74; A01N 25/34; C08K 5/09; C08K 5/10
[52] U.S. Cl. ................ 523/122; 424/78.31; 424/411; 524/140; 524/145; 524/267; 524/269; 524/287; 524/296; 524/299; 524/314; 524/321; 524/322; 524/569; 119/860
[58] Field of Search .................. 424/78.31, 411; 523/122; 524/140, 145, 296, 314, 569, 321, 322, 287, 299, 267, 269

[56] References Cited

U.S. PATENT DOCUMENTS

| | | | |
|---|---|---|---|
| 2,720,496 | 10/1955 | Bushnell | 524/296 |
| 3,852,416 | 12/1974 | Grubb et al. | 424/14 |
| 3,876,762 | 4/1975 | Rabussier et al. | 424/400 |
| 3,904,746 | 9/1975 | Aries | 424/411 |
| 4,150,109 | 4/1979 | Dick et al. | 424/411 |
| 4,250,838 | 2/1981 | Ott | 424/28 |
| 5,319,000 | 6/1994 | O'Connor et al. | 523/122 |
| 5,437,869 | 8/1995 | Kelley | 424/406 |

FOREIGN PATENT DOCUMENTS

| | | | |
|---|---|---|---|
| 656141 | 2/1992 | Australia . | |
| 649888 | 4/1993 | Australia . | |
| 662179 | 5/1993 | Australia . | |
| 0 539 295 A1 | 4/1993 | European Pat. Off. . | |
| 0 582 823 A1 | 2/1994 | European Pat. Off. . | |
| 33 00579 A1 | 7/1983 | Germany . | |
| 0021294 | 5/1974 | Japan | 524/496 |
| 86-064917 | 1/1986 | Japan . | |
| 5-194102 | 8/1993 | Japan . | |
| 5-221802 | 8/1993 | Japan . | |
| 5-301801 | 11/1993 | Japan . | |
| 181237 | 7/1978 | New Zealand . | |
| 186180 | 3/1987 | New Zealand . | |
| 236676 | 3/1992 | New Zealand . | |
| 237311 | 1/1993 | New Zealand . | |
| 1336495 | 11/1973 | United Kingdom . | |
| 2114442 | 8/1983 | United Kingdom . | |

*Primary Examiner*—Peter A. Szekely
*Attorney, Agent, or Firm*—Birch, Stewart, Kolasch & Birch, LLP

[57] ABSTRACT

Provided are a resin composition improved in utilization of active compound by controlling the bleeding of the active compound low in vaporizability and a molded product obtained from the resin composition. The resin composition comprises 100 parts by weight of a resin, 0.01–200 parts by weight of an active compound and 0.1–100 parts by weight of a vaporizable plasticizer having a vapor pressure of 0.001 mmHg or higher at 20° C., and the vapor pressure (P1) of the vaporizable plasticizer at 20° C. and the vapor pressure (P2) of the active compound at 20° C. satisfy the formula: $P1/P2 \geq 2$.

18 Claims, 1 Drawing Sheet ated products at the starting of use) before the active compound develops its inherent effect, and, as a result, the period during which the molded product releases the active compound becomes shorter than desired or the active compound is no longer released from the molded product at the desired time. Thus, there is the possibility of causing reduction in the utilization of the active compound.

RESIN COMPOSITION HAVING ACTIVE COMPOUND AND VAPORIZABLE PLASTICIZER, AND MOLDED PRODUCT THEREOF

BACKGROUND OF THE INVENTION

1. Field of the Invention

The present invention relates to a resin composition which provides a molded product in which the rate of an active compound having low vaporizability to be released from the molded product has been controlled and the utilization of the active compound contained therein been improved and further relates to the molded product obtained from the resin composition. More particularly, it relates to a resin composition which provides a molded product which stably retains therein the active compound under sealed condition and releases a suitable amount of the active compound under opened condition and, thus, is improved in utilization of the active compound and to the molded product obtained from the resin composition.

2. Description of the Related Prior Art

Resin compositions containing an active compound in the resin and molded products made from the compositions have, hitherto, been known and have been used in a wide variety of fields because molded products of various shapes can be relatively inexpensively obtained. According to these known art, the active compound is slowly released from the molded product by vaporization or oozing to the surface of the molded product, namely, so-called bleeding and the active compound exhibits its effect.

In the case of the active compound being low in vaporizability, the active compound is hardly released by vaporization, but is mainly released by bleeding. The bleeding occurs when the compound is retained in the molded product in an amount more than saturation dissolving amount (supersaturation amount) in the molded product and it is a phenomenon that the supersaturation portion (=amount of the added active compound—the saturation dissolution amount of the compound in the molded product) migrates to the surface of the molded product with lapse of time until the supersaturation portion reaches the surface. Therefore, in the case of a molded product obtained from a resin composition containing an active compound in an amount exceeding the saturation dissolution amount, the active compound bleeds to the surface of the molded product with lapse of time, but since the saturation dissolution amount of the active compound in the resin is fixed, it is generally difficult to control the bleeding rate or the starting time of bleeding of the active compound from the molded product. Furthermore, since the active compound in an amount less than the saturation dissolution amount can be relatively stably retained in the resin, substantially no active compound is released from the molded product after the supersaturation portion has bled.

Moreover, in the case of a molded product obtained from a resin composition containing an active compound in an amount more than the saturation dissolution amount, the active compound of the supersaturation portion is also released with time during storage and preservation of the molded product, which causes bleeding to the surface of the molded product or staining of the surface of other materials with which the molded product contacts during storage or preservation. This is not preferred. Further, if the active compound of the supersaturation portion is released during storage or preservation, the active compound sticks to the materials other than the targets (e.g., package of the molded products, hands of the person who equips the molded products at the starting of use) before the active compound develops its inherent effect, and, as a result, the period during which the molded product releases the active compound becomes shorter than desired or the active compound is no longer released from the molded product at the desired time. Thus, there is the possibility of causing reduction in the utilization of the active compound.

As a result of the intensive research, the inventors have found that a resin composition which comprises a resin containing an active compound and a vaporizable plasticizer gives a molded product which is controlled in the bleeding starting time and the bleeding rate of the active compound low in vaporizability. Thus, the present invention has been accomplished.

SUMMARY OF THE INVENTION

The present invention provides a resin composition which comprises 100 parts by weight of a resin, 0.01–200 parts by weight of an active compound and 0.1–100 parts by weight of a vaporizable plasticizer having a vapor pressure of 0.001 mmHg or higher at 20° C., the vapor pressure (P1) of the vaporizable plasticizer at 20° C. and the vapor pressure (P2) of the active compound at 20° C. satisfying the formula: $P1/P2 \geq 2$, and further provides a molded product obtained from the resin composition.

The present invention relates to a resin composition which gives a molded product, characterized by being controlled in the starting time of bleeding of an active compound or the bleeding rate of the active compound.

DESCRIPTION OF THE INVENTION

Figure 1:
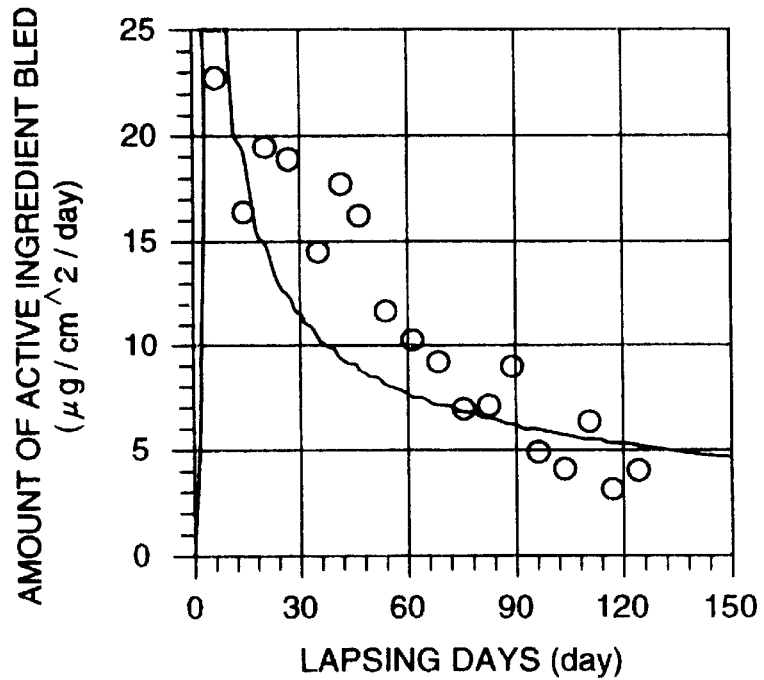
FIG. 1 and FIG. 2 show the change of bleeding amount of the active ingredient with lapse of time in Example 12.

In the present invention, the vaporizable plasticizer has the effect to retain stably the active compound in the resin composition, and, as a result, the saturation dissolution amount of the active compound in the resin composition increases than that in the resin. On the other hand, under opened condition, the vaporizable plasticizer vaporizes from the resulting molded product, and with decrease of the content of the vaporizable plasticizer in the molded product, the saturation dissolution amount of the active compound in the molded product decreases.

That is, in the present invention, the saturation dissolution amount of the active compound in the resin composition refers to the maximum amount of the active compound which can be dissolved in the resin composition. Accordingly, in the present invention, the saturation dissolution amount of the active compound in the resin composition increases by the action of the vaporizable plasticizer, and, under sealed condition, bleeding of the active compound from the molded product obtained from the resin composition is inhibited. On the other hand, under opened condition, the saturation dissolution amount of the active compound in the molded product decreases with vaporization of the vaporizable plasticizer, and, as a result, there can be realized the peculiar releasing behavior that the active compound in supersaturated state bleeds from the molded product. The sealed condition here is such a condition that an environment where vaporization of the vaporizable plasticizer from the molded product is inhibited can be attained, and, for example, such condition can be attained by sealing the molded product with a gas barrier material.

The vaporizable plasticizer used in the present invention is an organic compound having a vapor pressure of at least 0.001 mmHg at 20° C. From the point of further acceleration of bleeding of the active compound from the molded product, an organic compound having a vapor pressure of 0.01 mmHg or higher is more preferred and an organic compound having a vapor pressure of 0.1 mmHg or higher is most preferred. The upper limit of the vapor pressure of the vaporizable plasticizer is not critical, but from the viewpoint of processability, it is generally preferred that the boiling point of the plasticizer is higher than a melt molding temperature of the resin composition. From this viewpoint, the upper limit of the vapor pressure of the the vaporizable plasticizer is usually 100 mmHg, and 10 mmHg or lower is preferred from the point of processability and 1 mmHg or lower is especially preferred. Furthermore, it is more preferred that the plasticizer has a good compatibility with the resin and the active compound from the point of the effect to more stably retain the active compound in the resin composition as aforementioned.

The compatibility can also be expressed in the term such as dissolvability or miscibility and is an important factor which determines (saturation) solubility. The degree of compatibility or (saturation) solubility can be presumed from solubility parameter or dielectric constant, but the following measuring methods can be mentioned which are generally known. The solubility in polyvinyl chloride can be determined by repeating bleeding test using a test sheet comprising the resin, the vaporizable plasticizer and the active compound under the condition where the vaporizable plasticizer does not vaporize (reference literature: "Polyvinyl Chloride—The Basis and the Application—", pages 356–357 (1988) edited by Kinki Kagaku Kyokai, Vinyl Bukai and published from Nikkan Kogyo Shinbunsha). The solubility in polyolefin resins and other resins can also be determined by the similar method.

The vaporizable plasticizer can be selected from esters which are liquid at room temperature (23° C.) (hereinafter sometimes referred to as merely "liquid"), liquid alcohols, liquid ketones, perfumes, animal and plant essential oils, and the like. As examples of the liquid esters, mention may be particularly made of phthalic esters, straight chain dibasic acid esters, phosphoric esters, and the like. Examples of suitable vaporizable plasticizers used in the present invention are dimethyl adipate, dimethyl glutarate, dimethyl succinate, dimethyl phthalate, diethyl phthalate, triethyl phosphate, tributyl phosphate, dimethyl maleate, and the like.

Amount of the vaporizable plasticizer is 0.1–100 parts by weight, more preferably 1–50 parts by weight, further preferably 5–30 parts by weight for 100 parts by weight of the resin from the viewpoint of more stable retention of the active compound in the resin composition and the viewpoint of the effect that the plasticizer can be more stably retained in the resin composition.

The active compound used in the present invention is an organic compound having activity for insect control and insecticidal action, acaricidal action, repellency, bacteriocidal and fungicidal action, stainproofing, herbicidal action, plant growth regulation, dermal therapy, rust proofing, lubrication, anti-blocking, surface activity, antistatic action, and the like. The compound can be used each alone or in combination of two or more. The vapor pressure of the active compound used in the present invention is unlimited as far as it satisfies the relation with the vapor pressure of the vaporizable plasticizer mentioned hereinafter, but from the point of prevention of vanishment of the active compound due to vaporization at the step of (melt) processing of the resin composition, the vapor pressure at 20° C. is preferably lower than 0.01 mmHg, more preferably lower than 0.001 mmHg and organic compounds of low vaporizability having a vapor pressure of lower than 0.0001 mmHg are further preferred.

When an insect controlling or insecticidal active compound is used as the active compound, examples of the insect controlling or insecticidal active compound are various insecticidal active compounds, insect growth regulating active compounds, and the like.

Those compounds (synergists) having an action to increase the effect of the insect controlling compounds may be used in combination.

As these insecticidal active compounds, there may be used at least one compound selected from normally used insecticides such as pyrethroid compounds, phenylpyrazole compounds, organic phosphorus compounds, carbamate compounds, juvenile hormone compounds, and the like. Specific examples of the pyrethroid compounds are Permethrin, Allethrin, d-Allethrin, dd-Allethrin, Prallethrin, Cyphenothrin, Fenothrin, d-Fenothrin, d-Resmethrin, Empenthrin, Fenvalerate, Fenpropathrin, Cyhalothrin, Cyfluthrin, Etofenprox, Tralomethrin, Esbiothrin, Transfluthrin, Terallethrin and the like. Specific examples of the organic phosphorus compounds are Fenitrothion, Naled, Fenthion, Cyanophos, Chlorpyrifos, Diazinon, Calclofos, Salithion and the like. Specific examples of carbamate compounds are methoxadiazon, Propoxur, Carbaryl, Fenobcarb, and the like. Specific examples of the insect growth regulating compounds are Methoprene, Hydroprene, Diflubenzuron, Cyromazine, Fenoxycarb, lufenuron and the like. Specific examples of the synergists are piperonylbutoxide, Sainepirin, octachlorodipropyl ether, and the like.

As examples of acaricidal active compounds, mention may be made of acaricides such as trifluoro-methanesulfonic acid anilide compounds, pyrethroid compounds, and the like.

The repellency active compounds are compounds having an effect to repel insects and the like, and examples are repellents such as N,N-diethyl-m-triamide, carane-3,4-diol, and the like.

As the bacteriocidal and fungicidal and stainproofing active compounds, mention may be made of bacteriocides, fungicides and stainproofing agents, for example, isothiazoline compounds such as N-phenyl-benzisothiazolone-3, pyridylpyrimidine compounds such as 4,6-dimethyl-2-(6-phenylpyridin-2-yl)pyrimidine, oxonic acid, and Vinyzene.

As active compounds for herbicidal action, plant growth regulation, dermal therapy, rust proofing, lubrication, antiblocking, surface activity, antistatic action, mention may be made of commercially available herbicides, plant growth regulators, rust proofing agents, lubricants, anti-blocking agents, surface active agents, antistatic agents, and the like.

The combination of the vaporizable plasticizer and the active compound used in the present invention satisfies the formula: $P1/P2 \geq 2$ (wherein P1 denotes the vapor pressure of the vaporizable plasticizer at 20° C. and P2 denotes the vapor pressure of the active compound at 20° C.). In case of $P1/P2<2$, since the difference in vapor pressure of the vaporizable plasticizer and that of the active compound is small, the effect of peculiar releasing behavior of the active compound from the molded product, namely, the above-mentioned bleeding of the active compound under the opened condition becomes small. For further increase of the effect of the peculiar releasing behavior, the ratio of P1 and P2 is more preferably P1/P2≧5, and further preferably P1/P2≧10. The upper limit of P1/P2 is not critical, but usually is $10^{10}$.

The ratio of the amount of the vaporizable plasticizer and that of the active compound is optionally determined depending on the desired bleeding characteristics and the purpose for use. For example, in order to realize the adjustment of timing at which the bleeding of the active compound starts, the amount can be determined in the following manner. That is, in order for the bleeding of the active compound starting just after beginning of use, the ratio of the amount of the vaporizable plasticizer to that of the active compound may be set at low so that concentration of the active compound in the resin composition becomes supersaturated only when the vaporizable plasticizer slightly vaporizes. Furthermore, in order for the bleeding of the active compound starting after lapse of some period of time from beginning of use, the ratio of the amount of the vaporizable plasticizer to that of the active compound may be set at high so that concentration of the active compound in the resin composition does not become supersaturated unless a certain amount of the vaporizable plasticizer vaporizes. The saturation solubility of the active compound in the resin can be obtained by the same method as for obtaining the saturation solubility of the vaporizable plasticizer mentioned above. The decrement (vaporization amount) of the vaporizable plasticizer caused by vaporization can be obtained, for example, by previously measuring the change with time of the residual amount of the vaporizable plasticizer in the molded product.

Adjustment of the timing at which bleeding of the active compound starts can also be performed by changing the vapor pressure of the vaporizable plasticizer in addition to the above-mentioned method of changing the ratio of the amount of the vaporizable plasticizer and that of the active compound. That is, for early starting of bleeding of the active compound, a vaporizable plasticizer of higher vapor pressure can be used, and for late starting, a vaporizable plasticizer of lower vapor pressure can be used. Moreover, the timing at which bleeding of the active compound starts can also be adjusted by the amount of bleeding accelerator referred to hereinafter. Adjustment of bleeding rate can also be attained by these methods.

When the pseudostationary assumption of Higuchi et al (reference literature: Higuchi et al, "J. Pharm. Sci.", vol.50, 874 (1961)) is applied, the bleeding rate of the active compound in the present invention is proportional to the surface area of the molded product, the square root of diffusion coefficient of the active compound and the supersaturated portion of the active compound. In view of this information, when the bleeding rate of the active compound is to be controlled, for example, when the bleeding rate is to be increased, the supersaturated portion of the active compound can be increased. Furthermore, it is also possible to increase the bleeding rate by using a vaporizable plasticizer of high vaporization rate, for example, a vaporizable plasticizer having a high vapor pressure.

As the resin used in the present invention, there can be used those which are suitable for the active compounds used and suitable for use. Specific examples are polyolefins such as polyethylene, polypropylene, and copolymers of ethylene and organic carboxylic acid derivatives having an ethylenically unsaturated bond such as ethylene-vinyl acetate copolymer and ethylene-methyl methacrylate copolymer, thermoplastic resins such as polyvinyl chloride, polyvinyl alcohol, polycarbonate, polyester, polystyrene, and polymethyl methacrylate, thermosetting resins such as polyurethane and epoxy resin, synthetic rubbers such as styrene-butadiene rubber (SBR) and ethylene propylene terpolymer (EDPM), and the like.

Among these resins, from the point of enhancement of bleeding rate, more preferred are those which are high in movability of molecular chains low in glass transition temperature, and cause no chemical reaction with active compound. Especially, thermoplastic resins are superior in shapability and economical efficiency and, further, solubility and diffusibility of the active compound can be controlled in a wide range by proper selection of the thermoplastic resins and additives. Thus, they are more preferred as materials for the control of bleeding of the active compound. Furthermore, it is preferred to select the thermoplastic resins capable of being molded at lower than the decomposition temperature or boiling point of the active compound and the vaporizable plasticizer in order to inhibit the loss of the active compound or the vaporizable plasticizer caused by decomposition, vaporization to environment and dissolution into cooling water of the active compound or the vaporizable plasticizer when the resin composition of the present invention is molded.

The resin composition of the present invention may further optionally contain a bleeding accelerator, a plasticizer other than the above-mentioned vaporizable plasticizer (sometimes referred to as merely "plasticizer"), a stabilizer, a filler, a colorant, and the like in consideration of their compatibilities. Among them, the bleeding accelerator and the plasticizer can be suitably used for obtaining the activity more effectively by improving the bleeding properties of the active compound or improving the spreading effect of the bled active compound. The bleeding accelerator can be used to improve bleedability of the active compound, and can be suitably used for increasing diffusibility of the active compound in the case of the diffusibility of the active compound in the resin composition being low.

As the bleeding accelerator, preferred are those which are higher in diffusibility in the resin composition, lower in solubility in the resin composition and higher in solubility in the vaporizable plasticizer. Especially, carboxylic acids are preferred as the bleeding accelerator, and typical examples thereof are fatty acids such as lauric acid, myristic acid, palmitic acid and stearic acid, aromatic carboxylic acids such as benzoic acid, dicarboxylic acids such as tartaric acid, fumaric acid and malic acid, and tricarboxylic acids such as citric acid. Further examples are silicone compounds such as polydimethylsiloxane and polymethylphenylsiloxane, fluorine-based surface active agents, and phosphoric esters such as triphenyl phosphate disclosed in JP-A 5-194102.

The amount of the bleeding accelerator can be optionally set depending on the timing at which bleeding of the active compound starts, but is usually 0.1–100 parts by weight, more preferably 1–50 parts by weight, further preferably 5–20 parts by weight for 100 parts by weight of the resin.

In the case of using resins such as polyvinyl chloride, polyester, and polyvinyl alcohol as the resin in the resin composition of the present invention, plasticizers ordinarily used for imparting flexibility and processability may be added to the resin composition. Furthermore, when resins such as polyvinyl chloride which have a high dissolvability for the active compound are used, it is especially preferred to use plasticizers having a vapor pressure of lower than 0.0001 mmHg and low in compatibility with the resin. By using such plasticizer low in compatibility with the resin, it can be expected to provide the effect to lower the saturation solubility of the active compound in the resin composition and further enhance the bleedability of the active compound. As such plasticizers, mention may be made of, for example, diisononyl adipate, diisodecyl adipate, di-2-ethylhexyl azelate, 2-ethylhexyl sebacate, epoxidized soybean oil, aliphatic polyesters, etc. which are known as plasticizers low in compatibility with polyvinyl chloride resin.

The amount of these plasticizers is usually 0.1–200 parts by weight, preferably 5–100 parts by weight, more preferably 20–60 parts by weight for 100 parts by weight of the resin.

The method of addition of the active compound, the vaporizable plasticizer and the like to the resin is not limited. For example, they can be mixed using mixing machines such as Banbury mixer, super mixer and extruder to obtain a resin composition in the form of powder or pellet.

Furthermore, the active compound and the vaporizable plasticizer may be added to the molded product by previously molding a molded product containing neither the active compound nor the vaporizable plasticizer by the method mentioned hereinafter and immersing the resulting molded product in a liquid comprising the active compound and the vaporizable plasticizer or coating it with the liquid to absorb the active compound and the vaporizable plasticizer into the molded product.

The shape and molding method of the molded product of the present invention are not limited as far as it is obtained from the above-mentioned resin composition. The composition is processed into various shapes such as rod, plate, mesh, circle, sphere, triangle, half-round etc. depending on the use conditions, objects and uses, for example, as animal collars, ear tags, medals, etc. or nets, fibers, nonwoven fabrics, sheets, films, etc. The ear tags here are insect controlling articles to be attached to ears of domestic animals which control the insect pests which come flying to the animals, thereby to maintain the animals at healthy state. The molding method includes known methods such as, for example, injection molding, extrusion molding, powder molding and press molding. Moreover, the resin composition can be processed by various known methods employed for thermoplastic resins, such as multi-layer extrusion molding, multi-color injection molding, composite spinning and extrusion laminate molding depending on the purposes such as improvement of mechanical properties in use, increase of concentration of the active compound in the surface part of the molded product and improvement of processability. In the case of multi-layer extrusion molding and multi-color injection molding, the resin composition of the present invention may be applied to any layers.

The use and the method of use of the molded product of the present invention are unlimited, and it can be especially suitably used in the use and environment where the active compound of low vaporizability is relatively difficult to release. For example, depending on the activity of the active compound or purpose for use of the molded product, the molded product can be used for obtaining insect controlling and insecticidal activity, fungicidal and acaricidal activity, stain proofing activity, herbicidal activity, plant growth regulating activity, dermal therapeutic activity, rust proofing activity, lubricating activity, anti-blocking activity, surface activity, antistatic activity, and the like. For example, it can be used in anti-stick films containing a surface active agent, antistatic films containing an antistatic agent, insect controlling equipments for animals containing an insect controlling active ingredient (such as insect controlling collars for animals, insect controlling ear tags for animals, etc.) or the like.

Especially, since the molded product of the present invention can be properly adjusted in the timing at which the insect controlling active ingredient bleeds therefrom and is high in utilization of the insect controlling active ingredient, the higher insect controlling effect can be obtained by attaching to animals the insect controlling collars, insect controlling ear tags, insect controlling medals, and the like which are obtained by molding the resin composition of the present invention.

The present invention can be more suitably applied to active compounds of low vaporizability. Furthermore, according to the present invention, the peculiar releasing behavior can be realized that under sealed conditions, the active compound is stably retained in the resin composition and during use under opened conditions, the active compound bleeds with vaporization of the vaporizable plasticizer, and, thus, utilization of the active compound can be improved and the excellent activity can be obtained stably for a long period of time. Moreover, the timing at which bleeding of the active compound starts can be adjusted.

As mentioned above, the present invention attains controlled release of the active compound from the molded product due to bleeding. The ultimate object of the controlled release is to further enhance the effect of the active compound by releasing the active compound at a desired time, to a desired place and in a desired amount. Many methods have been proposed for attaining the controlled release, but according to the present invention, the controlled release can be attained by using a molded product obtained from a resin composition in which the active compound and the vaporizable plasticizer are uniformly dispersed and the present invention can provide a simple and economically superior method of controlled release.

The following nonlimiting examples will explain the present invention in more detail.

EXAMPLE 1

The starting materials were introduced into a supermixer at about 30° C., gradually heated to 130° C. and cooled to about 80° C. to obtain a powdered resin composition having the formulation as shown in Table 1. Then, the composition was kneaded for 5 minutes using a roll heated at 160° C. to obtain a sheet. The resulting sheet was pelletized by a sheet pelletizer. The resulting pellets were press molded at a molding temperature of 180° C. to obtain a sheet of 8 cm in length, 5.2 cm in width and 3 mm in thickness (having a surface area of about 91 $cm^2$). This sheet was suspended for 3 days in a circulation type oven set at 35° C. under opened condition and, then, the ingredient which bled to the surface was wiped off with a paper (Kimwipe manufactured by Jujo Kimbury Co., Ltd.) and accurately weighed by a scale to obtain the bleeding amount of the ingredient under the opened condition.

Simultaneously, the sheet was subjected to aging at 35° C. for 3 days in such a state as sealed with an aluminum foil and thereafter the ingredient which bled to the surface and the ingredient which adhered to the aluminum foil were wiped off in the same manner as above and accurately weighed to measure the bleeding amount under the sealed condition. Furthermore, in order to know the appearance during storage at high temperatures, the appearance of the sheet after stored in sealed state at 50° C. for 3 days was visually observed.

The results of these tests are shown in Table 3. Bleeding in a large amount was seen as compared with the result of Comparative Example 1 under the opened condition while under the sealed condition, bleeding in only a slight amount was seen and the appearance of the sheet stored in the sealed state was good.

EXAMPLE 2

In the same manner as in Example 1, except that the formulation was as shown in Table 1, the bleeding amount was measured after carrying out the aging at 35° C. for 3 days under opened condition and sealed condition. Furthermore, appearance of the sheet stored at 50° C. for 3 days in the sealed state was visually observed. The results are shown in Table 3. Bleeding in a larger amount as compared with the results of Comparative Examples 2 and 3 under opened condition was seen while, under sealed condition, bleeding in only a slight amount was seen and the appearance of the sheet stored in the sealed state was good.

COMPARATIVE EXAMPLES 1–3

In the same manner as in Example 1, except that the formulations were as shown in Table 1, the bleeding amount was measured after carrying out the aging at 35° C. for 3 days under opened condition and sealed condition. Furthermore, appearance of the sheet stored at 50° C. for 3 days in the sealed state was visually observed. The results are shown in Table 3. Bleeding was seen under the opened condition and bleeding in nearly the same amount was also seen under opened condition, and the appearance of the sheet stored in the sealed state was bad and a large amount of the ingredient adhered to the aluminum foil used as a wrapping material.

COMPARATIVE EXAMPLE 4

In the same manner as in Comparative Example 3, except that DOA which was a plasticizer higher in compatibility than DIDA was used in place of DIDA, the bleeding amount was measured after carrying out the aging at 35° C. for 3 days under opened condition and sealed condition. Furthermore, appearance of the sheet stored at 50° C. for 3 days in the sealed state was visually observed. The results are shown in Table 3. Substantially no bleeding was seen under both the opened condition and the sealed condition.

EXAMPLES 3–8

A powdered resin composition having the formulation as shown in Table 2 was obtained using a supermixer. Then, the powder was injection molded at a molding temperature of 180° C. to obtain a molded product in the form of an animal collar of 35 cm in length, 1 cm in width and 3 mm in thickness (having a surface area of about 91 cm$^2$). In the same manner as in Example 1, the resulting molded product was subjected to aging at 35° C. for 3 days under opened condition and sealed condition and the bleeding amount was measured. Furthermore, appearance of the molded product stored at 50° C. for 3 days in the sealed state was visually observed. The results are shown in Table 3. Bleeding in a larger amount under the opened condition was seen while, under the sealed condition, bleeding in only a slight amount was seen and the appearance of the molded product stored in the sealed state was good.

COMPARATIVE EXAMPLE 5

In the same manner as in Example 3, except that the formulation was as shown in Table 2, the bleeding amount was measured after carrying out the aging at 35° C. for 3 days under opened condition and sealed condition. Furthermore, appearance of the sheet stored at 50° C. for 3 days in the sealed state was visually observed. The results are shown in Table 3. Bleeding was seen under the opened condition, but bleeding in nearly the same amount was also recognized under the opened condition, and the appearance of the sheet stored in the sealed state was bad.

EXAMPLE 9

The molded product used in Example 6 was subjected to aging at 23° C. and 35° C. for 28 days, during which bleeding amount was measured every 7 days. The results are shown in Table 4. When the bled ingredient was repeatedly wiped off, bleeding in a large amount as compared with Comparative Example 5 was seen under the opened condition and bleeding in only a slight amount was seen under the sealed condition. The composition of the ingredient which bled after aging of 14 days under the opened condition was analyzed by gas chromatography to find SUM 32%, DIDA 56% and isostearic acid 12% at 23° C. and SUM 30%, DIDA 58% and isostearic acid 12% at 35° C.

COMPARATIVE EXAMPLE 6

The molded product used in Comparative Example 5 was subjected to aging at 23° C. and 35° C. for 28 days, during which the bleeding amount was measured every 7 days. The results are shown in Table 5. When the bled ingredient was repeatedly wiped off, bleeding was seen under the opened condition, but bleeding in nearly the same amount was also seen under the sealed condition. The appearance of the sheet stored in the sealed state was bad, and a large amount of the ingredient adhered to the aluminum foil used as a wrapping material. The bleeding amount when the ingredient was repeatedly wiped off tended to decrease. The composition of the ingredient which bled after aging of 14 days under the opened condition was analyzed by gas chromatography to find SUM 31% and DIDA 69% at 23° C. and SUM 36% and DIDA 64% at 35° C.

TABLE 1

|  |  | Example 1 | Comparative Example 1 | Example 2 | Comparative Example 2 | Comparative Example 3 | Comparative Example 4 |
|---|---|---|---|---|---|---|---|
| Resin (parts by weight) | Resin A | 100 | 100 | 100 | 100 | 100 | 100 |
| Active compound (parts by weight) | EXM | 47 | 47 | 32 | 32 | 32 | 32 |
| Vaporizable plasticizer | DBAM | 55 | 0 | 0 | 0 | 0 | 0 |
| (parts by weight) | TEP | 0 | 0 | 20 | 0 | 0 | 0 |
| Plasticizer | DIPA | 0 | 0 | 55 | 55 | 55 |  |
| (parts by weight) | DOA |  |  |  |  |  | 55 |

TABLE 1-continued

|  |  | Example 1 | Comparative Example 1 | Example 2 | Comparative Example 2 | Comparative Example 3 | Comparative Example 4 |
|---|---|---|---|---|---|---|---|
| Bleeding accelerator (parts by weight) | Stearic acid | 5 | 5 | 10 | 10 | 0 | 0 |
| Stabilizer (parts by weight) | 0–130P | 5 | 5 | 5 | 5 | 5 | 5 |
|  | LBZ-793L | 2.5 | 2.5 | 2.5 | 2.5 | 2.5 | 2.5 |
|  | Barium stearate | 0.4 | 0.4 | 0.4 | 0.4 | 0.4 | 0.4 |
| Calorant (parts by weight) | Titanium oxide | 1.14 | 1.14 | 1.14 | 1.14 | 1.14 | 1.14 |

TABLE 2

|  |  | Example 3 | Comparative Example 5 | Example 4 | Example 5 | Example 6 | Example 7 | Example 8 |
|---|---|---|---|---|---|---|---|---|
| Resin | Resin A | 90 | 90 | 90 | 90 | 90 | 90 | 90 |
| Resin (parts by weight) | Resin B | 10 | 10 | 10 | 10 | 10 | 10 | 10 |
| Active compound (parts by weight) | EXM | 0 | 0 | 0 | 0 | 0 | 0 | 0 / 28.9 |
|  | SUM | 32 | 32 | 32 | 32 | 32 | 28.9 | 0 |
|  | SLV | 0 | 0 | 0 | 0 | 0 | 4.6 | 4.6 |
| Vaporizable plasticizer (parts by weight) | TEP | 20 | 0 | 20 | 20 | 20 | 19 | 19 |
| Plasticizer Bleeding (parts by weight) | DIDA | 55 | 55 | 55 | 55 | 55 | 55 | 55 |
| Bleeding accelerator (parts by weight) | Stearic acid | 10 | 0 | 0 | 0 | 0 | 0 | 0 |
|  | Myristic acid | 0 | 0 | 10 | 0 | 0 | 0 | 0 |
|  | Palmitic acid | 0 | 0 | 0 | 10 | 0 | 0 | 0 |
|  | Isostearic acid | 0 | 0 | 0 | 0 | 10 | 10 | 10 |
| Stabilizer (parts by weight) | 0–130P | 5 | 5 | 5 | 5 | 5 | 5 | 5 |
|  | LBZ-793L | 2.5 | 2.5 | 2.5 | 2.5 | 2.5 | 2.5 | 2.5 |
|  | Barium stearate | 0.4 | 0.4 | 0.4 | 0.4 | 0.4 | 0.4 | 0.4 |

TABLE 3

|  | Bleeding amount after 3 days at 35° C. (mg/91 cm$^2$) | | Ratio: (Bleeding amount under opened condition/bleeding amount under sealed condition) | Appearance after stored at 50° C. for 3 days in sealed state |
|---|---|---|---|---|
|  | Opened condition | Sealed condition | | |
| Example 1 | 42.6 | 0.1 | 426 | Good |
| Comparative Example 1 | 28.1 | 30.0 | 1 | Bad |
| Example 2 | 129.0 | 1.7 | 76 | Good |
| Comparative Example 2 | 101.9 | 108.5 | 1 | Bad |
| Comparative Example 3 | 21.2 | 36.1 | 1 | Bad |
| Comparative Example 4 | 2.1 | 1.8 | 1 | Good |
| Example 3 | 33.0 | 3.0 | 11 | Good |
| Comparative Example 5 | 26.0 | 31.0 | 1 | Bad |
| Example 4 | 156.0 | 12.0 | 13 | Good |
| Example 5 | 33.1 | 1.2 | 28 | Good |
| Example 6 | 34.0 | 0.9 | 38 | Good |
| Example 7 | 117.3 | 1.0 | 117 | Good |
| Example 8 | 124.3 | 1.3 | 96 | Good |

TABLE 4

Change of bleeding amount in Example 9

| The number of wiping | Lapsing days | Aging at 23° C. | | | Aging at 35° C. | | |
|---|---|---|---|---|---|---|---|
|  |  | Opened condition | Sealed condition | Ratio | Opened condition | Sealed condition | Ratio |
| 1 | 7 | 25.2 | 1.1 | 23 | 63.6 | 2.3 | 28 |
| 2 | 14 | 27.7 | 2.8 | 10 | 64.8 | 2.6 | 25 |

TABLE 4-continued

Change of bleeding amount in Example 9

| The number of wiping | Lapsing days | Aging at 23° C. | | | Aging at 35° C. | | |
|---|---|---|---|---|---|---|---|
| | | Opened condition | Sealed condition | Ratio | Opened condition | Sealed condition | Ratio |
| 3 | 21 | 27.0 | 2.6 | 10 | 75.3 | 2.5 | 30 |
| 4 | 28 | 31.4 | 4.7 | 7 | 77.8 | 2.8 | 28 |
| Total | | 111.3 | 11.2 | 10 | 281.5 | 10.2 | 28 |

TABLE 5

Change of bleeding amount in Comparative Example 6

| The number of wiping | Lapsing days | Aging at 23° C. | | | Aging at 35° C. | | |
|---|---|---|---|---|---|---|---|
| | | Opened condition | Sealed condition | Ratio | Opened condition | Sealed condition | Ratio |
| 1 | 7 | 6.6 | 6.3 | 1 | 42.5 | 42.5 | 1 |
| 2 | 14 | 4.6 | 4.8 | 1 | 37.6 | 33.6 | 1 |
| 3 | 21 | 4.0 | 4.3 | 1 | 31.6 | 30.8 | 1 |
| 4 | 28 | 4.0 | 3.8 | 1 | 30.2 | 34.1 | 1 |
| Total | | 19.2 | 19.2 | 1 | 141.9 | 141.2 | 1 |

EXAMPLE 10

In the same manner as in Example 7, except that the amount of isostearic acid was 8 parts, the bleeding amount (mg/91 cm$^2$) was measured every 3 days at 35° C. The results are shown in Table 6.

EXAMPLE 11

Example 10 was repeated, except that the amount of isostearic acid was 4 parts. The results are shown in Table 6.

TABLE 6

Change of bleeding amount at 35° C. (mg/91 cm$^2$)

| The number of wiping | Lapsing days | Opened condition | | Sealed condition | |
|---|---|---|---|---|---|
| | | Example 10 | Example 11 | Example 10 | Example 11 |
| 1 | 3 | 101 | 3 | 1.5 | 1.4 |
| 2 | 6 | 124 | 65 | 0.8 | 0.3 |
| 3 | 9 | 88 | 71 | 1.1 | 0.6 |

In Example 10, the bleeding was seen already after lapse of 3 days under the opened condition while in Example 11, no bleeding was seen after 3 days and the bleeding was seen after 6 days. As can be seen from comparison of Example 10 and Example 11, controlled release could be realized by reducing the amount of the bleeding accelerator.

EXAMPLE 12

A resin molded product of the present invention was obtained in the same manner as in Example 7, except that the amount of isostearic acid was 6 parts.

This molded product showed excellent effect as a collar for animals.

Figure 2:
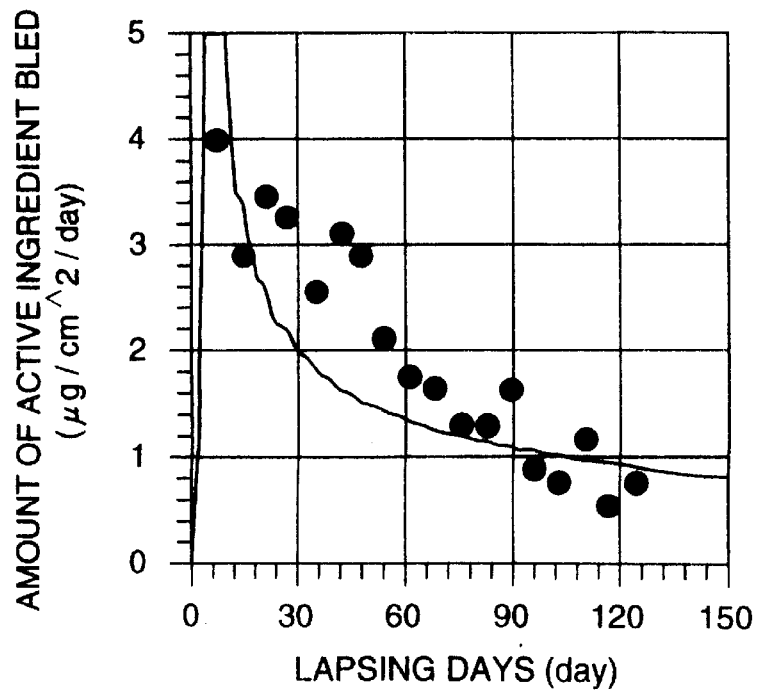

Furthermore, this molded product was suspended in a circulation type thermostatic chamber kept at 35° C. and both sides of the specimen were wiped with a paper (Kimwipe manufactured by Jujo Kimbury Co., Ltd.) every about 1 week. The paper was then subjected to extraction with methanol, and the extract was diluted and subjected to quantitative analysis of the active ingredient by a liquid chromatograph to measure the bleeding amount at the time of repeated wiping. Change with time of the amount of Sumithrin and Sumilav which bled to the surface of the collar is shown in FIG. 1 and FIG. 2. The bleeding amount was calculated by dividing the amount determined by the liquid chromatograph by the surface area (91 cm$^2$) and the days lapsing from the preceding wiping (7 days in principle).

Since bleeding of the active ingredient was seen continuously for about 4 months, it is considered that the molded product is effective for more than 4 months as insect controlling articles such as collars, ear tags and medals for animals.

Main materials used in Examples and Comparative Examples are as follows:

<Resins>

Resin A: Polyvinyl chloride [Sumilit (average polymerization degree: 1300; suspension polymerization product) manufactured by Sumitomo Chemical Co., Ltd.]

Resin B: Polyvinyl chloride ["Sumilit" (average polymerization degree: 1100; emulsion polymerization product) manufactured by Sumitomo Chemical Co., Ltd.]

<Active compound>

Permethrin: ["Exmine" (EXM) having a vapor pressure of 5.5×10$^{-7}$ mmHg at 20° C. and manufactured by Sumitomo Chemical Co., Ltd.]

d-Fenothrin: ["Sumithrin" (SUM) having a vapor pressure of 1.2×10–6 mmHg at 20° C. and manufactured by Sumitomo Chemical Co., Ltd.]

Pyriproxyfen: ["Sumilav" (SLV) having a vapor pressure of 2.2×10–6 mmHg at 20° C. and manufactured by Sumitomo Chemical Co., Ltd.]

<Vaporizable plasticizer>

Mixed methyl ester of succinic acid, glutaric acid and adipic acid (abbreviated as DBAM; having a vapor pressure of 0.1 mmHg at 20° C. and manufactured by Sanken Kako Co., Ltd.)

Triethyl phosphate ("TEP" having a vapor pressure of 0.3 mmHg at 20° C. and manufactured by Kurogane Kasei Co., Ltd.)

<Plasticizer>

Diisodecyl adipate (abbreviated as DIDA; having a vapor pressure of 1×10–7 mmHg at 20° C. and manufactured by Sanken Kako Co., Ltd.)

Di-2-ethylhexyl adipate (abbreviated as DOA; having a vapor pressure of 7×10–7 mmHg at 20° C. and manufactured by Sanken Kako Co., Ltd.)

<Stabilizer>

O-130P: Epoxidized soybean oil manufactured by Asahi Denka Kogyo K.K. and used also as a secondary plasticizer LPZ-793L: Liquid barium-zinc based stabilizer manufactured by Sakai Kagaku Co., Ltd.

EXAMPLE 13

A powdered resin composition having the formulation as shown in Table 7 was obtained using a supermixer. Then, the powder was injection molded at a molding temperature of 150° C. to obtain a molded product in the form of an animal collar of 35 cm in length, 1 cm in width, 3 mm in thickness (having a surface area of about 91 cm$^2$). In the same manner as in Example 1, the molded product was subjected to aging at 35° C. for 3 days under opened and sealed conditions and the bleeding amount was measured. Further, appearance of the molded product stored at 50° C. for 3 days in the sealed state was visually observed. The results are shown in Table 8. Bleeding in a large amount was seen under the opened condition while under the sealed condition bleeding in only a slight amount was seen and appearance of the sheet stored in the sealed state was good.

TABLE 7

|  |  | Example 13 |
|---|---|---|
| Resin | Resin C | 90 |
| (parts by weight) | Resin B | 10 |
| Active compound | BAK | 28.2 |
| (parts by weight) | SLV | 4.5 |
| Vaporizable plasticizer | TEP | 20 |
| (parts by weight) |  |  |
| Bleeding accelerator | Isostearic acid | 18 |
| (parts by weight) |  |  |
| Stabilizer | NF90 | 0.5 |
| (parts by weight) | NF915 | 0.5 |
|  | Nx-803A | 0.2 |
|  | 909 | 1.0 |
| Processing aid | Lub | 0.3 |
| (parts by weight) |  |  |

TABLE 8

|  | Bleeding amount after 3 days at 35° C. (mg/91 cm$^2$) | | Ratio: (Bleeding amount under opened condition/ bleeding amount under sealed condition) | Appearance after stored at 50° C. for 3 days in sealed state |
|---|---|---|---|---|
|  | Opened condition | Sealed condition |  |  |
| Example 13 | 44.2 | 0.5 | 88 | Good |

<Resin>

Resin C: Polyvinyl chloride [Sumilit (average polymerization degree: 800; suspension polymerization product) manufactured by Sumitomo Chemical Co., Ltd.]

<Active Compound>

Fenocarb: [Osbac (BAK) having a vapor pressure of 3.6×10$^{-4}$ mm Hg at 20° C., manufactured by Sumitomo Chemical Co., Ltd.; a carbamate compound]

<Stabilizer>

Bis(2,2,6,6-tetramethyl-4-piperidinyl) sebacate: (NF 90 manufactured by Nissan Ferro Co., Ltd.) 4,4'-Isopropylidenedihenolalkyl (C$_{12}$–C$_{15}$) phosphite: (NF 915 manufactured by Nissan Ferro Co., Ltd.)

Mixture of bis(2,2,6,6-tetramethyl-4-piperidinyl)sebacate and n-octadecyl-β-(4'-hydroxy 3',5'-t-butylphenyl) propionate: (Nx-803A manufactured by Nissan Ferro Co., Ltd.)

Bisphenol A diglycidyl ether: (909 manufactured by Nissan Ferro Co., Ltd.)

<Processing Aid>

Low-molecular weight polyethylene: (Lub manufactured by Nissan Ferro Co., Ltd.)

What is claimed is:

1. A resin composition consisting essentially of
   100 parts by weight of a resin,
   0.01–200 parts by weight of an active compound,
   0.1–100 parts by weight of a vaporizable plasticizer having a vapor pressure of 0.001 mmHg or higher at 20° C., and
   0.1–100 parts by weight of a bleeding accelerator selected from the group consisting of a fatty acid, an aromatic carboxylic acid, a dicarboxylic acid, a tricarboxylic acid and a silicone compound,
   the vapor pressure (P1) of the vaporizable plasticizer at 20° C. and the vapor pressure (P2) of the active compound at 20° C. satisfying the formula: $P1/P2 \geq 2$.

2. A resin composition according to claim 1, wherein the vaporizable plasticizer is an ester which is liquid at room temperature (23° C.).

3. A resin composition according to claim 1, wherein the active compound has a vapor pressure of lower than 0.01 mmHg at 20° C.

4. A resin composition according to claim 3, wherein the active compound is at least one agent selected from the group consisting of insecticides, acaricides, repellents, bacteriocides, fungicides, stainproofing agents, herbicides, plant growth regulators, dermal therapeutic agents, rust proofing agents, lubricants, anti-blocking agents, surface active agents and antistatic agents.

5. A resin composition according to claim 3, wherein the active compound is at least one agent selected from the group consisting of insecticides, acaricides, repellents, bacteriocides, fungicides and stainproofing agents.

6. A resin composition according to claim 3, wherein the active compound is at least one active compound selected from the group consisting of pyrethroid compounds, organic phosphorus compounds, carbamate compounds and juvenile hormone compounds.

7. A resin composition according to claim 3, wherein the active compound is a pyrethroid compound and/or a juvenile hormone compound.

8. A resin composition according to claim 3, wherein the active compound is a carbamate compound and/or a juvenile hormone compound.

9. A resin composition according to claim 1, wherein the resin is polyvinyl chloride resin.

10. A resin composition according to claim 1, which additionally contains 0.1–200 parts by weight of a plasticizer having a vapor pressure of lower than 0.0001 mmHg at 20° C.

11. A resin composition according to claim 1, wherein the vapor pressure (P1) of the vaporizable plasticizer at 20° C. and the vapor pressure (P2) of the active compound at 20° C. satisfy the formula: $P1/P2 \geq 5$.

12. A molded product comprises the resin composition of claim 1.

13. A collar for animals which is obtained by molding the resin composition of claim 5.

14. An ear tag for animals which is obtained by molding the resin composition of claim 5.

15. A medal for animals which is obtained by molding the resin composition of claim 5.

16. A method for controlling the bleeding of the active compound using a molded product obtained by molding the resin composition of claim 1.

17. A method for control of insect pests of animals which comprises attaching to animals a collar obtained by injection molding the resin composition of claim 5.

18. The resin composition according to claim 1, wherein said vaporizable plasticizer is selected from the group consisting of dimethyl adipate, dimethyl glutarate, dimethyl succinate, dimethyl phthalate, diethyl phthalate, triethyl phosphate, tributyl phosphate and dimethyl maleate.

\* \* \* \* \*